(12) United States Patent
    Sumanasinghe

(10) Patent No.: US 10,596,364 B2
(45) Date of Patent: Mar. 24, 2020

(54) FLUID FLOW CONTROL SYSTEMS FOR MEDICAL APPLICATIONS

(71) Applicant: Cook Medical Technologies LLC, Bloomington, IN (US)

(72) Inventor: Ruwan Sumanasinghe, Carmel, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 118 days.

(21) Appl. No.: 15/662,130

(22) Filed: Jul. 27, 2017

(65) Prior Publication Data

US 2019/0030314 A1    Jan. 31, 2019

(51) Int. Cl.
    *A61M 39/28*    (2006.01)
    *A61M 39/24*    (2006.01)

(52) U.S. Cl.
    CPC ............ *A61M 39/28* (2013.01); *A61M 39/24* (2013.01); *A61M 2039/2453* (2013.01); *A61M 2039/2466* (2013.01)

(58) Field of Classification Search
    CPC .............. A61M 39/06; A61M 39/0606; A61M 39/0613; A61M 39/28; A61M 39/24; A61M 2039/2453; A61M 2039/2466; A61M 2039/2433; A61M 2039/2426; A61M 2039/246; A61M 2039/062; A61M 2039/06226; A61M 2039/0633; A61M 2039/064; A61M 2039/0653; A61M 2039/066; A61M 2039/0673; A61M 39/0693; A61M 39/22; A61M 2039/244; A61M 2039/2446; A61M 2039/027; A61M 2039/0626; A61M 2039/0646; A61M 2039/0666
    See application file for complete search history.

(56) References Cited

U.S. PATENT DOCUMENTS

| 4,610,665 | A | | 9/1986 | Matsumoto |
| 4,978,341 | A | * | 12/1990 | Niederhauser ...... A61M 25/013 604/256 |
| 5,125,904 | A | | 6/1992 | Lee |
| 5,176,652 | A | | 1/1993 | Littrell |
| 5,195,980 | A | | 3/1993 | Catlin |

(Continued)

FOREIGN PATENT DOCUMENTS

| EP | 1099456 | 5/2001 |
| EP | 2213327 | 8/2010 |

(Continued)

OTHER PUBLICATIONS

Extended European Search Report for 18275100.8 dated Sep. 25, 2018, 8 pgs.

(Continued)

*Primary Examiner* — Kami A Bosworth
*Assistant Examiner* — Leah J Swanson
(74) *Attorney, Agent, or Firm* — Brinks Gilson & Lione

(57) ABSTRACT

In one aspect, fluid flow control systems, such as for medical applications, may include a resistance barrier and a flexible ring that may receive a device. The resistance barrier may exert barrier forces on the device, and the flexible ring may exert ring forces on the device, in order to create a fluid tight seal.

20 Claims, 13 Drawing Sheets

(56) References Cited

U.S. PATENT DOCUMENTS

| | | | |
|---|---|---|---|
| 5,997,515 A * | 12/1999 | de la Torre | A61B 17/3417 |
| | | | 604/246 |
| 6,024,729 A | 2/2000 | Dehdashtian | |
| 6,090,067 A | 7/2000 | Carter | |
| 6,656,153 B1 * | 12/2003 | Sakai | A61M 25/0075 |
| | | | 604/164.13 |
| 7,731,695 B2 * | 6/2010 | McFarlane | A61B 17/3462 |
| | | | 604/167.06 |
| 7,914,491 B2 * | 3/2011 | Rockrohr | A61B 17/3462 |
| | | | 604/164.01 |
| 8,267,897 B2 | 9/2012 | Wells | |
| 8,790,309 B2 | 7/2014 | Goode | |
| 2001/0041872 A1 | 11/2001 | Paul, Jr. | |
| 2004/0172008 A1 | 9/2004 | Layer | |

FOREIGN PATENT DOCUMENTS

| | | |
|---|---|---|
| EP | 2870947 B1 | 4/2016 |
| WO | WO2014/153302 | 9/2014 |

OTHER PUBLICATIONS

Response to Written Opinion for European Application 18275100.8 filed Jul. 24, 2019, 15 pgs.

* cited by examiner

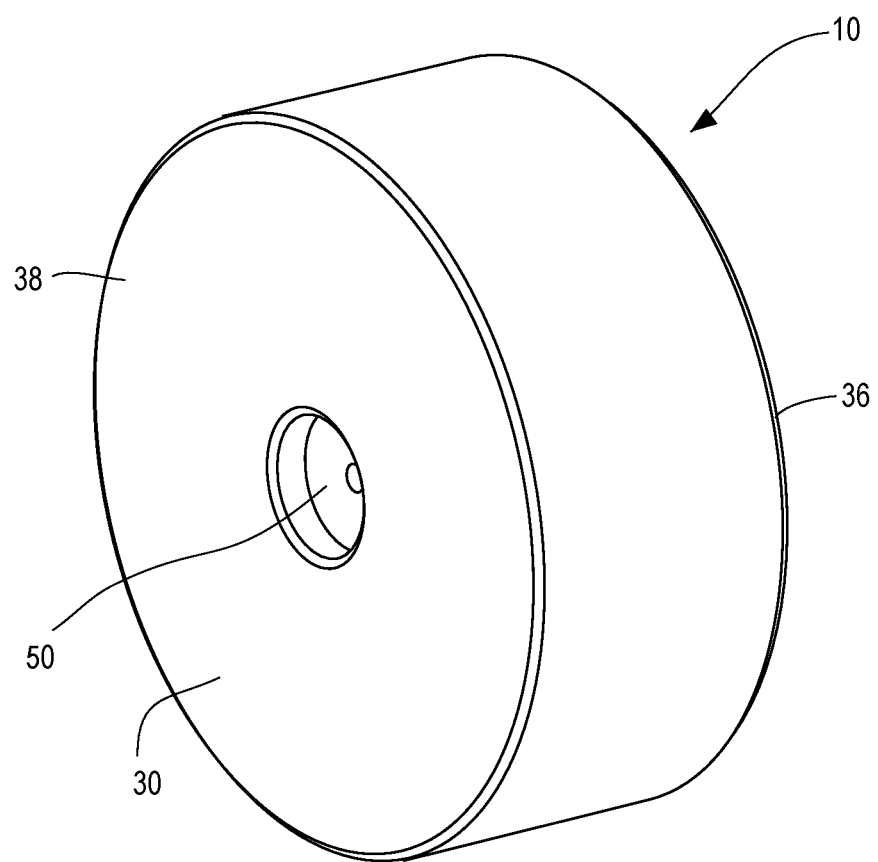

FLUID FLOW CONTROL SYSTEMS FOR MEDICAL APPLICATIONS

BACKGROUND

Medical procedures in a wide range of fields, including cardiology, endoscopy, vascular surgery, oncology, radiology, urology, electrophysiology, gynecology, otolaryngology, anesthesiology, gastroenterology, endocrinology, and numerous other fields frequently include the introduction of objects, such as instruments and devices, into a patient's anatomy. Common objects include needles, trocars, dilators, guide wires, catheters, cannulas, sheaths, balloons, stent grafts, and ablators, among many others. During such procedures, it is often desirable to minimize fluid loss, for example through the opening through which the above devices enter the patient's anatomy, and through the devices or instruments themselves.

For this purpose, medical devices and instruments commonly incorporate fluid flow control systems. Prior art fluid flow control systems may inadequately control fluid loss under certain conditions, for example during procedures requiring the introduction of devices with a range of diameters. Additionally, changes in material properties of prior art systems may lead to degraded performance during the course of a medical procedure. Additionally, prior art systems may require active input by a human operator, e.g., turning a handle, which introduces the possibility of errors or mishandling, leading to longer procedure times.

The fluid control systems disclosed herein address these known issues, and can be used in many medical applications that require fluid leakage control during the procedure. This application refers to devices, but it is to be understood that the invention may be readily practiced in the context of instruments and other objects without limitation.

SUMMARY

The disclosed embodiments relate to fluid flow control systems suitable for use in medical applications.

In one aspect, a fluid flow control system may include a housing and a flexible ring located within the housing, the flexible ring having an orifice for receiving a device. A resistance barrier may comprise at least one force element and may be adjacent to an exterior surface of the flexible ring. The resistance barrier may selectively exert a radially-inward barrier force upon the exterior surface of the flexible ring and towards the orifice. In another aspect, the resistance barrier may automatically exert the barrier force. In another aspect, the barrier force may be zero under certain conditions, such as when the fluid flow control system is in a first state. In another aspect, the flexible ring may exert a ring force. The ring force may be independent of the barrier force, may be less than the barrier force, and may be zero under certain conditions, such as when the fluid flow control system is in a first state. In another aspect, the fluid flow control system may include a first pad. The force element may create an attraction force between the first pad and a second pad, and the force element may form a physical connection between the first and second pads. The force element may include a magnet, a spring, an elastic component, a pneumatic cylinder, a hydraulic cylinder, or an electric actuator.

In another aspect, a flexible ring may have a surface defining an orifice, and an axis may pass through the orifice. A resistance barrier may be adjacent to the flexible ring and have at least one force element. A channel may be formed in a housing about the axis, and the channel may prevent movement of the flexible ring in directions parallel to the axis and may limit movement of the flexible ring in radial directions. In another aspect, the channel may have a substantially uniform cross section about the axis. In another aspect, the surface of the ring may be attached to the housing. In another aspect, the flexible ring may include a first band with a circumferential channel, and the resistance barrier may include a second band that resides within the circumferential channel. In another aspect, the surface of the flexible ring may enclose a filler material, which may comprise a polymer, or may include hyaluronic acid, polymethylmethacrylate, or polyacrylamide. In another aspect, the flexible ring and the resistance barrier may be concentrically assembled within the channel.

In yet another aspect, a method for controlling fluid flow during a medical procedure may include manipulating a device through an orifice of a flexible ring in at least a longitudinal direction and utilizing at least one force element, disposed external to the flexible ring, to automatically exert a radially-inward sealing force on the flexible ring. The sealing force provided by the at least one force element is transferred towards the orifice to provide a seal around the device. In another aspect, the method may include preventing movement of a portion of the flexible ring in the longitudinal direction and limiting movement of the flexible ring in a radially-outward direction.

The methods and systems disclosed herein are non-limiting and may be applied to other vasculature or anatomy. Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1B illustrates an isometric view of an embodiment of a fluid flow control system.

DETAILED DESCRIPTION OF THE EMBODIMENTS

Figure 1A:
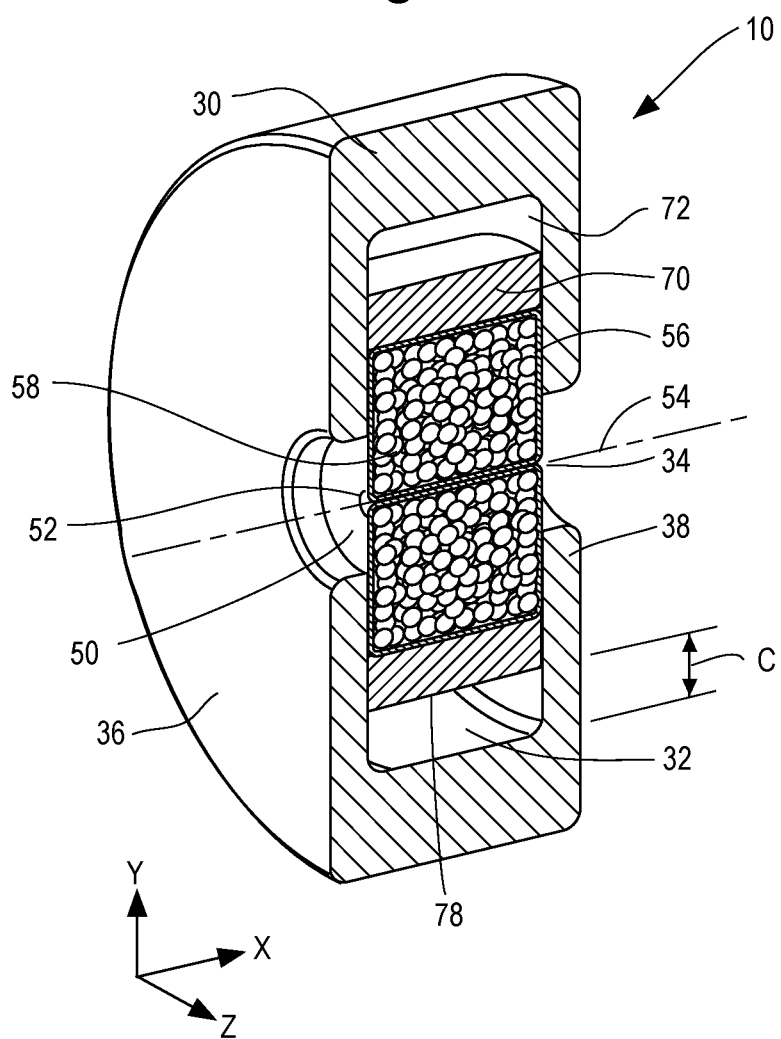
FIG. 1A illustrates a section view of an embodiment of a fluid flow control system, taken along an x-y plane.
Figure 1C:
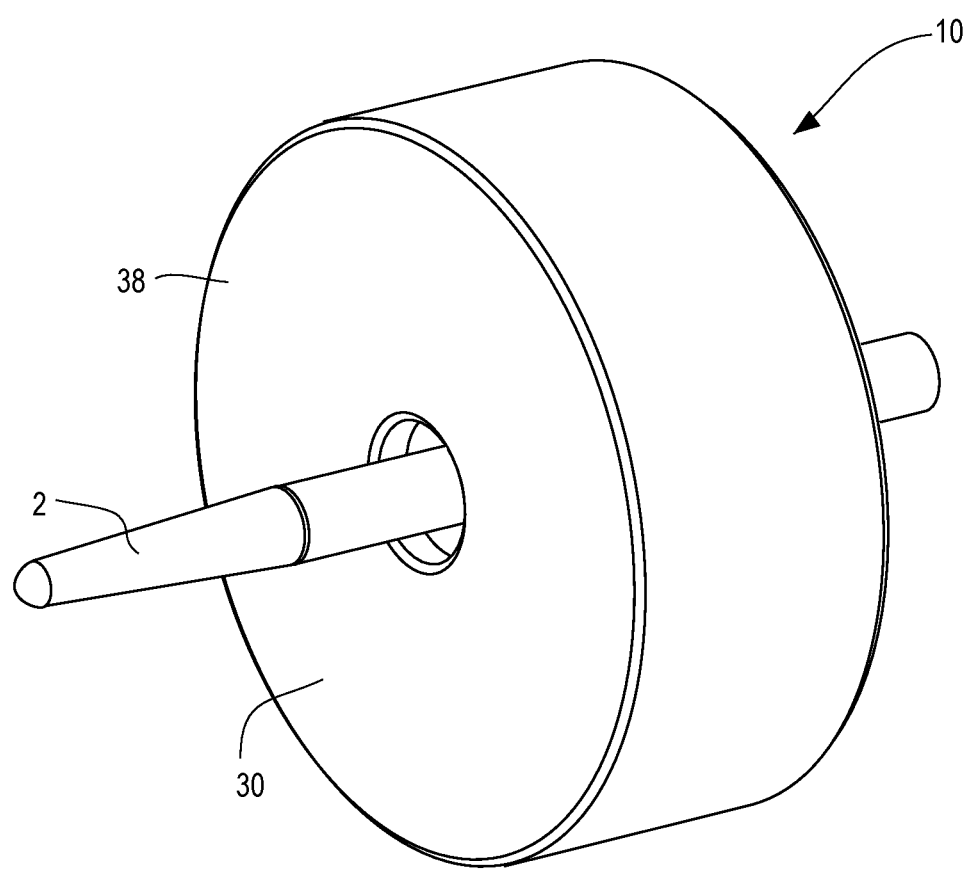
FIG. 1C illustrates an isometric view of an embodiment of a fluid flow control system, with a medical device inserted therethrough.
Figure 1D:
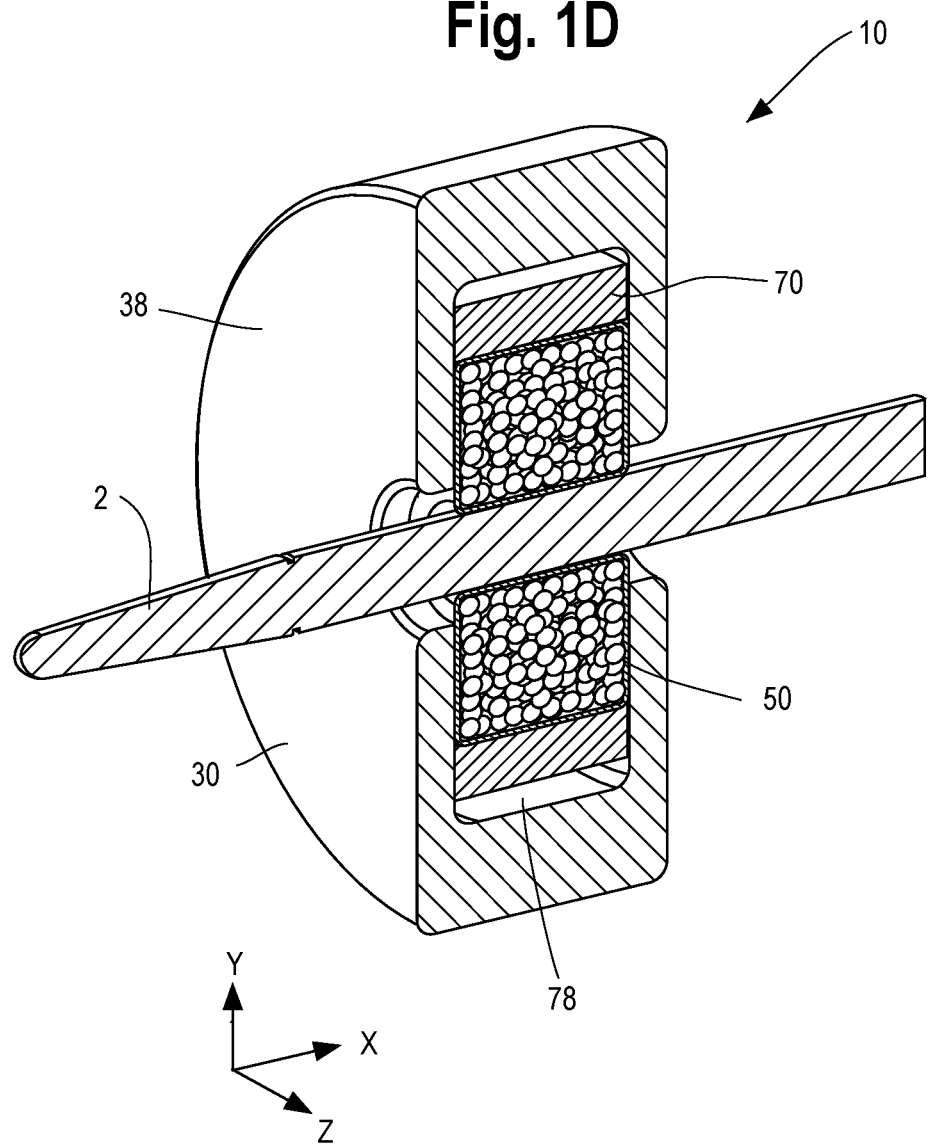
FIG. 1D illustrates a section view of an embodiment of a fluid flow control system, taken along an x-y plane, with a medical device inserted therethrough.

FIGS. 1A, 1D show sectional views of two embodiments of a fluid flow control system 10, taken along an x-y plane. The system may be integrated into a larger assembly, e.g., an introducer system, an intravenous infusion system, and a urology drainage system, and the system may be utilized in conjunction with a wide range of objects, for example medical devices including guide wires, catheters, needles, trocars, dilators, cannulas, sheaths, balloons, stent grafts, and ablators. The system includes a housing 30 and a flexible ring 50 defining an orifice 52. It may be helpful to envision an x-axis 54 passing through the orifice 52. The housing 30 may include a channel 32 formed about the x-axis 54, in which the flexible ring 50 resides. Optionally, one or more pads 70 may occupy at least part of a space 72 between the flexible ring 50 and the housing 30. The embodiments shown in FIGS. 1A-1D share common structural elements with the embodiments shown in FIGS. 2A-2D, but do not necessarily correspond exactly.

Figure 4:
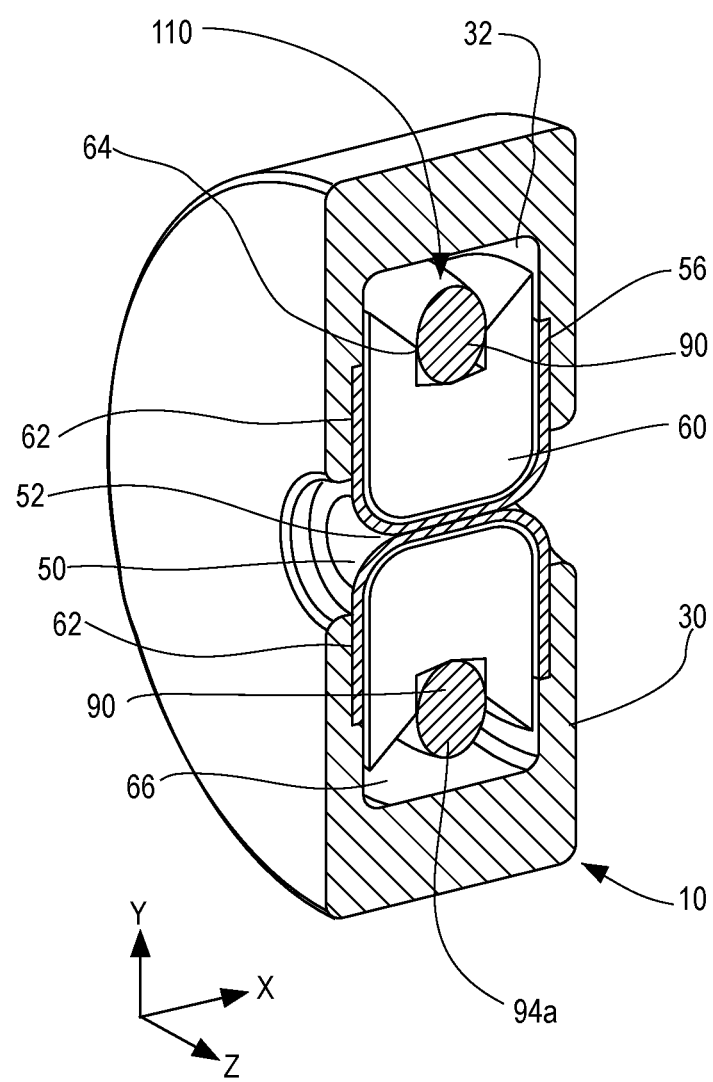
FIG. 4 illustrates a section view of another embodiment of a fluid flow control system, taken along an x-y plane.

FIGS. 2A-2D show sectional views of embodiments of fluid flow control systems 10 according to the present invention, taken along a y-z plane. The flexible ring 50, pad(s) 70, and housing 30 may form a concentric assembly about the x-axis 54. The embodiments in FIGS. 2A-2E each have a plurality of pads 70 occupying at least part of the space 72 between the flexible ring 50 and the housing 30, though alternative embodiments may not employ any pads 70 (as shown in FIG. 4), or may employ only a single pad 70 (not shown).

A force element 90 may be positioned adjacent to the flexible ring 50, a pad 70, and/or the housing 30. The force element 90 may exert forces on the flexible ring 50, such as a radially inward force, but need not exert a force directly upon the flexible ring 50, and need not exert a force at all times. Referring to FIGS. 2A-3B, the force element 90 may draw ends of one or more pads 70 together. Referring to FIG. 4, the force element 90 may exert a force on the flexible ring 50. Alternatively, the force element 90 may exert a force on an exterior surface of one or more pads 70 or exert a force through additional interactions. In all embodiments, the interaction between one or more force elements 90 and the flexible ring 50 cooperate to form a resistance barrier 110 that resists radially outward movement and deformation of the flexible ring 50.

With reference to FIGS. 1A-4, the housing 30 has an interior channel 32 formed about the x-axis 54 to accommodate the flexible ring 50 and other components of the fluid flow control system 10. The channel 32 may assume a number of shapes sufficiently large to accommodate the flexible ring 50 and resistance barrier components 110. In the embodiments of FIGS. 1A-4, the channel 32 generally has a substantially uniform cross section about the x-axis 54, such as a toroidal shape. However, the channel 32 may have a shape with a variable cross section, for example to accommodate additional components (not shown). The housing 30 provides a convenient vehicle to integrate the fluid flow control system 10 into other assemblies, and also to accommodate a range of movement and/or distortion of system components in radial directions relative to the x-axis 54, while preventing movement of system components the x-direction. In particular, the housing 30 may have an aperture 34 extending through a first surface 36 and a second surface 38 in the x-direction, the aperture 34 being sized at least large enough to circumscribe the orifice 52 of the flexible ring 50 in order to accommodate the insertion, removal, and manipulation of a medical device 2 through the orifice 52, as shown in FIGS. 1C-1D. The aperture 34 may be sized larger than the orifice 52 in order to accommodate a range of device diameters or to accommodate a range of movement of such devices in radial directions, but to limit radial movement beyond a predetermined threshold. Also, the first and second surfaces 36, 38 of the housing 30 prevent x-direction movement of at least a portion of the flexible ring 50 and other components located within the housing 30. This x-direction restriction enables the resistance barrier 110 to efficiently transfer barrier forces to the flexible ring 50, and further enables the flexible ring 50 to efficiently transfer the barrier forces and ring forces to devices inserted through the orifice 52. The aperture 34 may be circular or another shape, depending on the application. Suitable materials for the housing 30 include, but are not limited to, plastics such as polycarbonate, acrylic, polystyrene, acrylonitrile butadiene styrene (ABS), Delrin, and acetal.

Figure 2A:
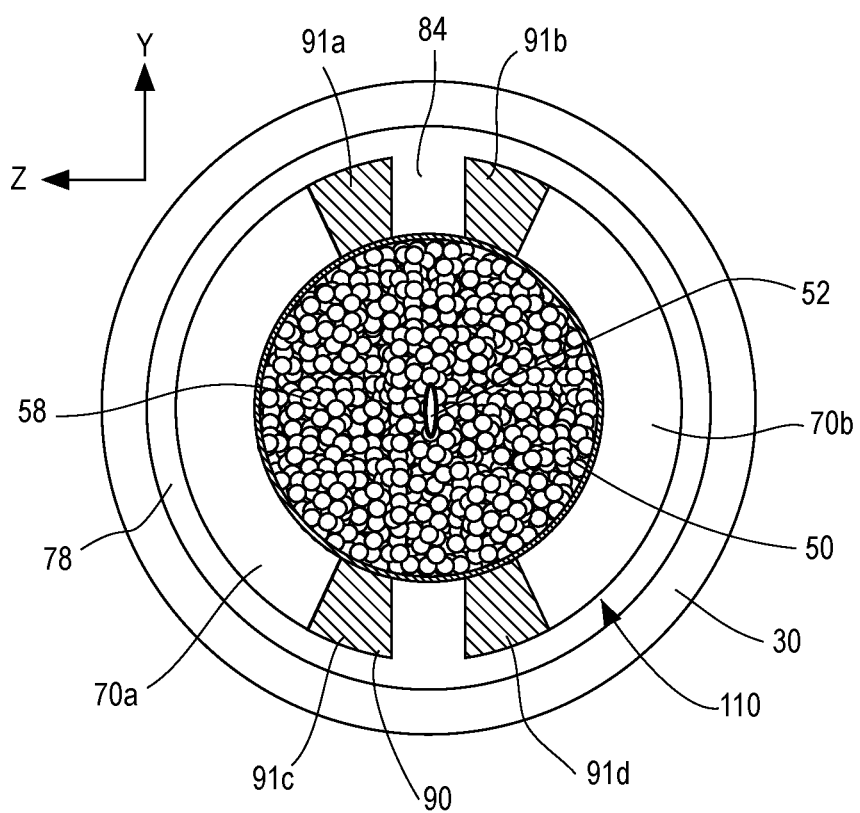
FIG. 2A illustrates a section view of another embodiment of a fluid flow control system, taken along a y-z plane.

As discussed above, the flexible ring 50 defines an orifice 52 and resides within a channel 32 of the housing 30. Specifically, the ring 50 has an exterior surface 56 that may be closed or open in one or more aspects. Exterior surface 56 may include a film, but need not be limited to a film and may include different and/or additional materials. The exterior surface includes all exterior surfaces of the ring 50, including radially outward surfaces, radially inner surfaces that define the orifice 52, and lateral surfaces. In embodiments where the exterior surface 56 is closed, such as in FIGS. 1A, 1D-2E, the exterior surface 56 may enclose a volume of filler material 58 or a filler element 60. In embodiments where the exterior surface 56 is open, such as in FIGS. 3A-4, the flexible ring 50 may comprise a filler element 60 or a separate element containing filler material 58 (not shown). Whether the exterior surface 56 is open or closed, it may be attached to other components of the fluid flow control system 10, for example the housing 30 as shown in FIGS. 3A-4. In such embodiments, the attachment interface 62 between the exterior surface 56 and other components may advantageously prevent movement of at least a portion of the flexible ring 50 in the x-direction. The attachment interface 62 may be formed from adhesive, heat treating, welding, and other suitable post-processing joining step known in the art. Alternatively, the exterior surface 56 may be attached to the other component via mechanical relationship, e.g., a tongue-and-groove relationship or other suitable joining method.

The exterior surface 56 of the flexible ring 50 may comprise a film such as, but not limited to, silicone elastomer, polyurethane or other appropriate elastomer with relatively high tear resistance and low friction surface properties. A surface coating may be applied on the exterior surface 56 of the flexible ring 50 to reduce the coefficient of friction between the flexible ring 50, pads 70, the housing 30, other components, and any devices inserted through the orifice 52. Suitable surface coatings include, but are not limited to, polyvinylpyrrolidone, hydrogel, and polytetrafluoroethylene.

The exterior surface 56 may have flexible properties that accommodate movement and stretching. Also, the exterior surface 56 may have slack that enables the orifice 52 to move radially by a slack amount without stretching the exterior surface 56. Also, the exterior surface 56 may have elastic properties, such that it exerts ring forces such as a reaction ring force opposite to a stretch direction. For example, if a device 2 inserted through the orifice 52 is moved radially outward and causes the exterior surface 56 to distort beyond an undistorted state, a trailing part of the exterior surface 56 may exert a ring force that tends to re-center the orifice 52. The ring forces may partially be a function of the material properties of the flexible ring 50, and may be independent from any barrier forces exerted by the resistance barrier 110. It may also be advantageous for the ring forces to differ from the barrier forces discussed below. For example, relatively low ring forces compared to the barrier forces may facilitate insertion, removal, and manipulation of devices within the orifice 52. However, it may be desirable for the ring forces to be sufficiently large to cause the orifice 52 to close in upon itself when free of any devices, in order to prevent fluid loss, for example without the assistance of any barrier forces, as shown in FIGS. 1A-1B, 2A-4.

In embodiments where the flexible ring 50 comprises a filler material 58 such as in FIGS. 1A, 2A-2C, the filler material 58 may have flexible properties that accommodate movement and stretching to a certain degree selected based on a particular application or procedure. Optionally, the filler material 58 may have elastic properties that are the same as or different from the exterior surface 56. For example, it may be advantageous for the filler material 58 to exert greater ring forces than the exterior surface 56 in order to reduce stress on the exterior surface 56 and the likelihood of tearing. Suitable filler materials 58 include, but are not limited to, hyaluronic acid, polymethylmethacrylate, polyacrylamide, or other hydrogels, or polymer spheres or polymeric fibers (e.g., fibers oriented concentrically to the orifice).

In other embodiments, the flexible ring 50 may comprise a solid filler element 60 instead of or in addition to filler material 58, for example a band that encircles the orifice. Referring to FIGS. 3A-4, such an element 60 may be continuous or an assembly of more than one component. Similar to the exterior surface 56 of the flexible ring 50 and filler material 58, the filler element 60 may have flexible properties to accommodate a range of movement, and may also have elastic properties to exert ring forces independently of the exterior surface 56 and filler material 58, for example reaction forces. Suitable materials for the filler element 60 include, but are not limited to, silicone elastomers or other elastomers with low hardness and high flexibility. The filler element 60 may have additional features, for example a channel 64 to accommodate a force element 90 or other component, as in FIG. 4.

A radially inner portion of the exterior surface 56 may define the orifice 52, or an insert that defines the orifice (not shown) may be joined with the exterior surface 56. If the exterior surface 56 defines the orifice, additional material may be provided near the orifice 52 to improve durability and tear resistance in that region. Alternatively, if an insert defines the orifice 52, the insert may be constructed of the same or different materials from the exterior surface 56. Suitable materials for the insert include silicone elastomer, polyurethane or other appropriate elastomer with sufficiently high tear resistance, high flexibility, and low frictional surface properties. The material or materials selected to form the region defining the orifice 52 should have flexible properties that allow the flexible ring 50 to accommodate a range of device diameters inserted there through by expanding or stretching.

A portion of the exterior surface 56 may have some slack that enables the orifice 52 to move within a limited range without stretching the exterior surface 56, such as when the orifice 52 receives a device 2 and a user manipulates the device 2 in a radial direction. Beyond this limited range of slack movement, further radial movement may cause the flexible ring 50 to stretch or distort, in particular the portion of the flexible ring 50 near the orifice 52. During such a movement or distortion, one part of the flexible ring 50 "leads," i.e., advances ahead of the device 2. Additionally, another part of the flexible ring 50 "trails," i.e., advances behind the device 2. Likewise, the device 2 would have leading and trailing parts. The leading and trailing parts of the flexible ring 50—in particular the parts of the exterior surface 56 that define the orifice 52—may move or distort together or independently in order to maintain a fluid-tight seal around the device 2. For example, the flexible ring 50 may exert a radially-inward ring force on the leading surface of the device 2 in order to resist radially-outward movement; simultaneously, the flexible ring 50 may exert a ring force on the trailing surface of the device 2 in order to maintain a fluid-tight seal around the device 2 during periods when the user manipulates the device radially. Depending on the location of the device 2, such ring forces may appear to act in radially inward or outward directions. Additional forces, such as barrier forces exerted by the resistance barrier, can augment the ring forces in this respect, causing the fluid flow control system 10 to maintain a fluid-tight seal around the surface of a device 2.

Referring to FIGS. 2A-4, at least one force element 90 may exert a force. The force element 90 and the flexible ring 50 may be concentrically assembled about the x-axis. In the embodiments shown in FIGS. 1A, 2A-2C, a plurality of force elements 90 draw together adjacent pads 70. In the embodiments of FIGS. 2D-F, a single force 90 element acts on the pads 70. In embodiments comprising pads 70, the pads 70 may transfer forces from the force element 90 to the flexible ring 50 and may distribute forces around the exterior surface 56 of the flexible ring 50, thereby causing a radially inward force to act upon the flexible ring 50. In embodiments with a plurality of pads 70, the force element 90 may draw ends of adjacent pads 70 together, i.e., create an attraction force between adjacent pads 70 (for example, as shown in FIGS. 2A-C, 3A-B), may exert a radially inward force on an exterior surface 74 of the pads 70 (for example, as shown in FIGS. 2D-2F), or may act on the pads 70 in another manner. In embodiments with a single pad 70, for example a ring-shaped pad 70 with spaced apart ends (not shown), the force element 90 may tend to draw adjacent ends 76 of the pad 70 together. In alternative embodiments, one or more force elements 90 may act directly on the flexible ring 50, as shown in FIG. 4.

The force elements 90 may comprise different force creating structures that provide specific advantages, including but not limited to magnets, springs, elastic components, pneumatic cylinders, hydraulic cylinders, and electric actuators. Referring to FIG. 2A, the force elements 90 may comprise magnets or magnetized components 91a-91d, e.g., magnets constructed from neodymium or samarium cobalt. Each magnet 91a-91d may be affixed to a pad 70, such as on the end 76 of the pad 70. Adjacent magnets positioned upon adjacent pads 70 may have opposite polarities in order to attract each other. In one example, depicted in FIG. 2A, a first magnet 91*a* coupled to pad 70*a* may comprise an opposite polarity relative to a second magnet 91*b* coupled to an adjacent pad 70*b*. Similarly, a third magnet 91*c* coupled to another end of the pad 70*a* may comprise an opposite polarity relative to a fourth magnet 91*d* coupled to an adjacent pad 70*b*. In such embodiments, the magnets 91*a*-91*d* draw the pads 70*a*-70*b* together, and the pads 70*a*-70*b* exert forces on the flexible ring 50, predominantly a radially inward force. Stronger or weaker magnets may be used to create different forces on the flexible ring 50, depending on the application.

Figure 2B:
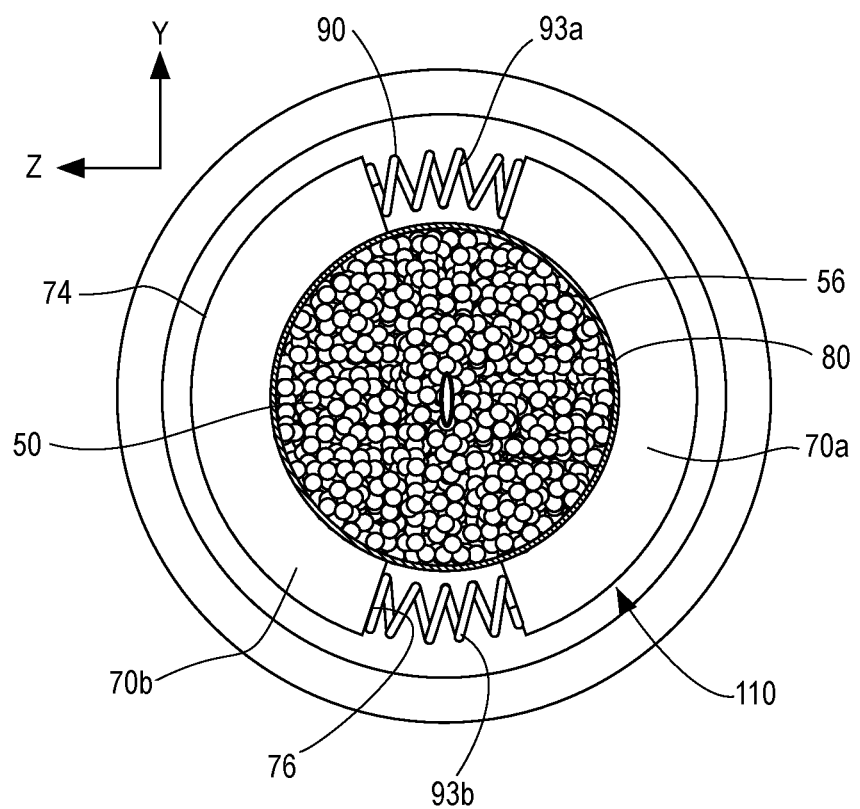
FIG. 2B illustrates a section view of yet another embodiment of a fluid flow control system, taken along a y-z plane.
Figure 2C:
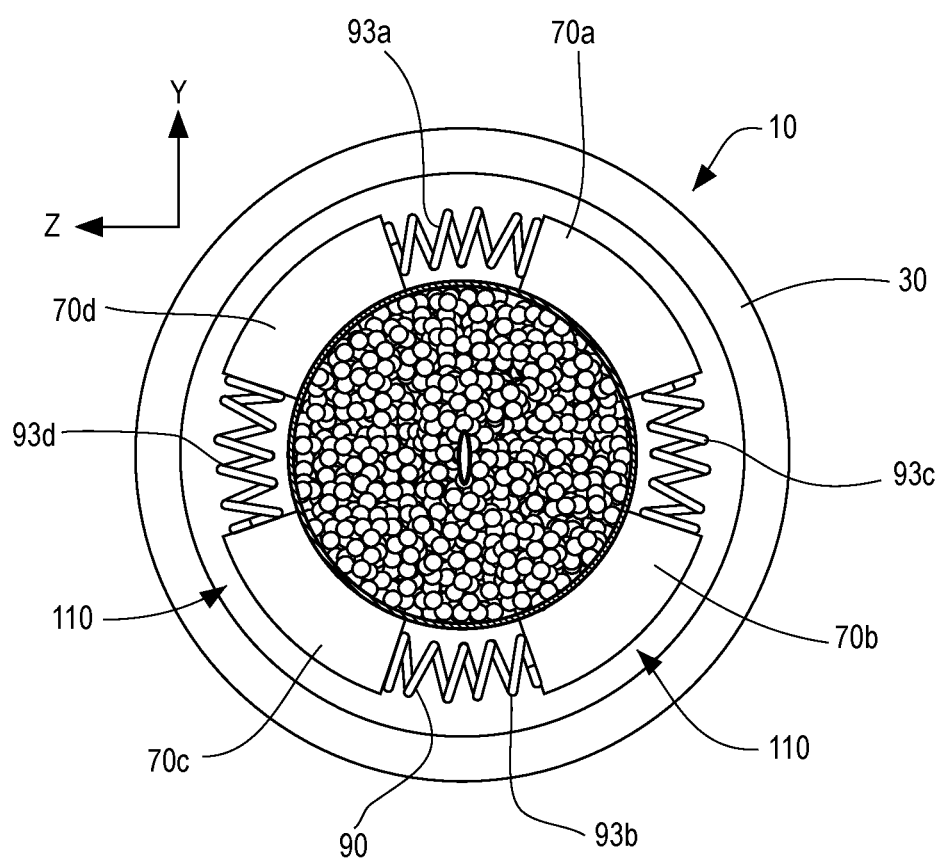
FIG. 2C illustrates a section view of yet another embodiment of a fluid flow control system, taken along a y-z plane.
Figure 3A:
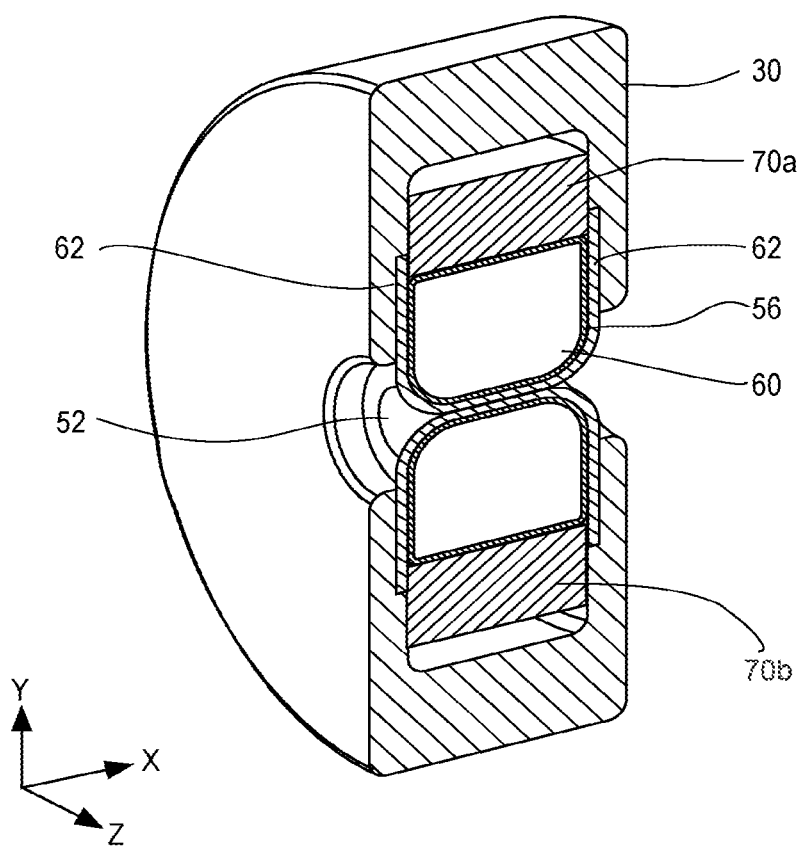
FIG. 3A illustrates a section view of another embodiment of a fluid flow control system, taken along an x-y plane.
Figure 3B:
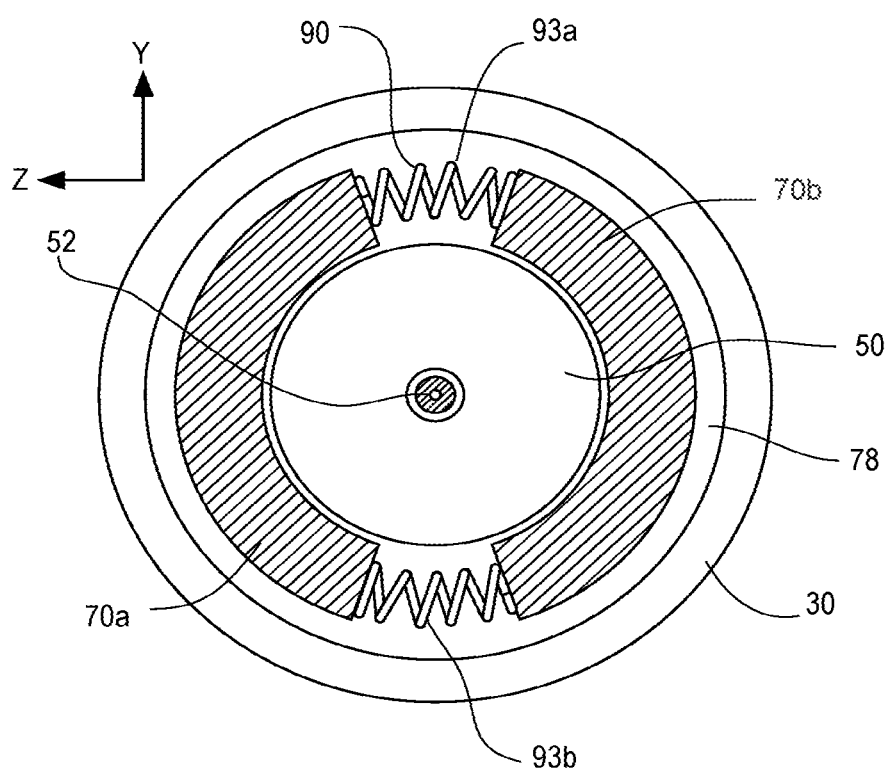
FIG. 3B illustrates another section view of the embodiment of FIG. 3A, taken along a y-z plane.

Referring to FIGS. 2B-2C and 3B, the force elements 90 may include springs 93*a*-93*d*, and may be physically attached to at least one pad 70, such as pads 70*a*-70*d*. In the embodiment of FIGS. 2B and 3B, two springs 93*a* and 93*b* are shown, where the spring 93*a* is coupled between upper surfaces of the pads 70*a* and 70*b*, and the other spring 93*b* is coupled between lower surfaces of the pads 70*a* and 70*b*. In the embodiment of FIG. 2C, four springs 93*a*-93*d* and four pads 70*a*-70*d* are shown. In these embodiments, each spring may draw adjacent pads 70*a*-70*b* together to indirectly exert forces on the flexible ring 50, including a radially-inward force. The forces may be adjusted by adjusting the number of springs, the spring constant k of each spring, or by adjusting the spring length 1 of each spring. Suitable spring materials include stainless steel and other steels.

Figure 2D:
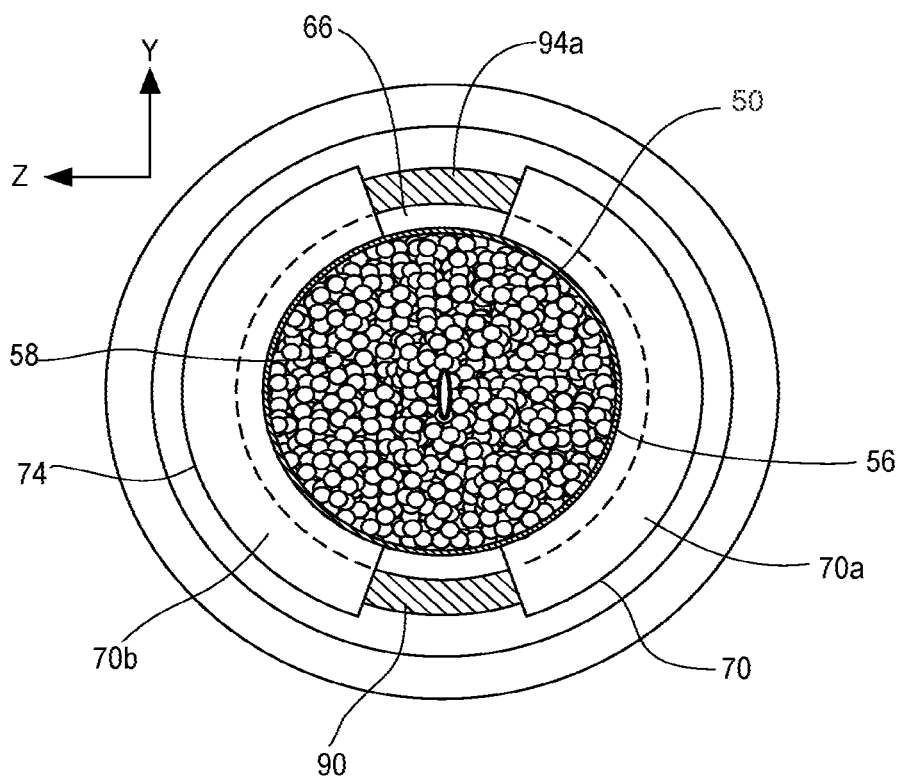
FIG. 2D illustrates a section view of yet another embodiment of a fluid flow control system, taken along a y-z plane.
Figure 2E:
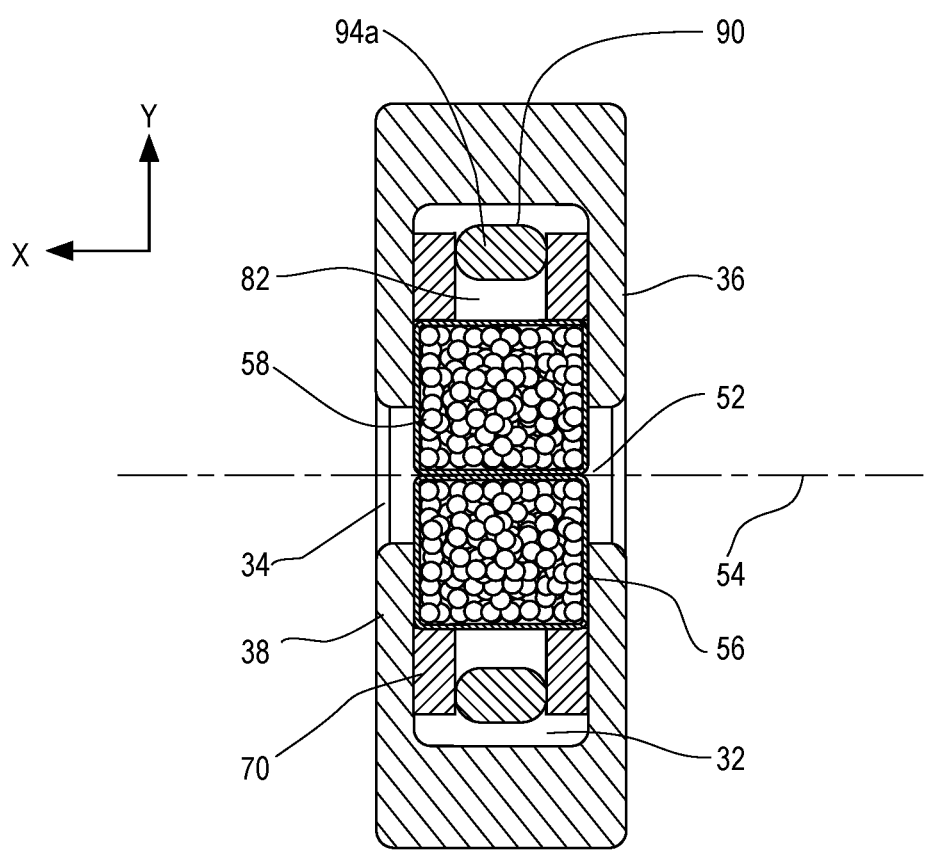
FIG. 2E illustrates another section view of the embodiment shown in FIG. 2D, taken along an x-y plane.
Figure 2F:
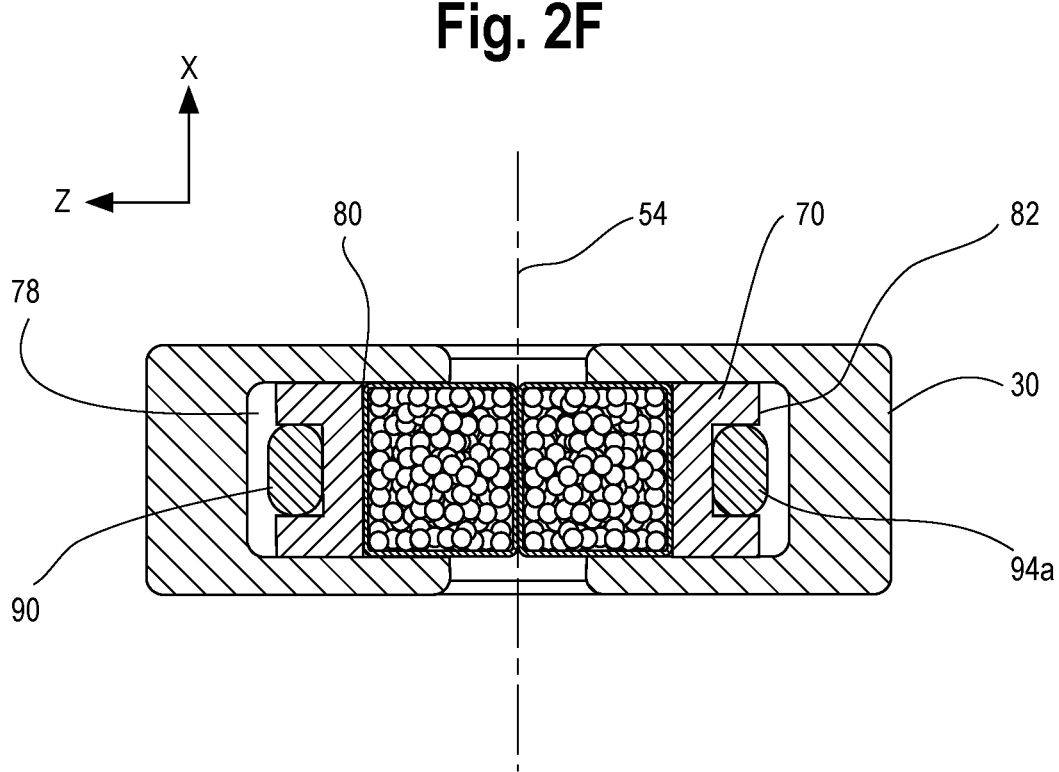
FIG. 2F illustrates another section view of the embodiment of FIGS. 2D-E, taken along an x-z plane.

Referring to FIGS. 2D-F and 4, the force element 90 may alternatively comprise one or more elastic elements 94*a* that exert a force on one or more pads 70 (as shown in FIGS. 2D-F) or directly on the flexible ring 50 (as shown in FIG. 4). The magnitude of the force may be adjusted by utilizing elastic elements with different cross sectional dimensions, different material properties, and different diameters. Suitable materials for the elastic element include, but are not limited to, silicone elastomers.

As discussed above, the fluid flow control system may feature at least one pad 70 occupying at least part of the space 72 between the flexible ring 50 and the housing 30. As shown in FIGS. 1A, 2A-3B, the pads 70 and flexible ring 50 may be concentrically positioned about the x-axis 54. The pad 70 and the housing 30 may be separated by a clearance 78 as shown in FIG. 1A. For example, the embodiments shown in FIGS. 1A, 2A-3B each feature a plurality of pads 70, as explained further above with respect to pads 70*a*-70*b* or alternatively pads 70*a*-70*d*. The number of pads 70 may vary depending on the required distribution and magnitude of the barrier forces. Alternative embodiments may not employ any pads 70 (for example, as shown in FIG. 4), or may employ only a single pad 70 (not shown), for example a single pad 70 extending nearly around the circumference of the ring, with two ends 76 separated by a gap. The pad or pads 70 may serve several functions. For example, the pad 70 may provide a means to redirect a force toward the flexible ring 50, such as a force generated by a force element 90. Also, the pad or pads 70 may redistribute a force around the flexible ring 50 so that the force is more evenly distributed. Also, by occupying at least a portion of a space 72 between the exterior surface 56 of the flexible ring 50 and the housing 30, the pad 70 may limit the amount that the flexible ring 50 may move or flex, especially in radial directions.

Referring to FIGS. 1A, 1D-3B, the pads 70 may have an arc or crescent shape with an inner surface 80 that corresponds with an outer portion of the exterior surface 56 of the flexible ring 50. A pad 70 may generally have a cross section that approximates the shape of the space 72 in which it resides within the housing 30. Referring to FIGS. 2E-2F, the pad 70 may include a channel 82, such as a circumferential channel, that cooperates with a force element 90, such as elastic element 94*a*. In alternative embodiments not shown, the pads 70 may have different shapes to conform to different flexible rings 50 and housings 30. Additionally, pads 70 may be integrally formed with, joined to, or abutting force elements 90, as shown in FIGS. 2A-2C.

In embodiments having a plurality of pads 70 as in FIGS. 1A, 1D-3B, adjacent pads 70 may be separated by a gap 84 at times. In other words, the pads 70 may be spaced sufficiently far apart from one another and sized in relation to the flexible ring 50 and housing 30 to permit relative movement. For example, adjacent pads 70 may be sufficiently spaced apart to enable force elements 90 to draw adjacent pads 70 toward one another at all times. Thus, it may be desirable for adjacent pads 70 to have sufficient spacing that they do not contact each other during normal operation of the fluid flow control system 10. Alternatively, pads 70 may be sized such that adjacent pads 70 remain in contact until separated by a radially outward force, such as a user might exert when manipulating a medical device 2 within the orifice 52. In such embodiments, the force elements 90 may not have any effect until radially outward movement or distortion exceeds a certain threshold. Suitable pad materials include, but are not limited to, relatively hard elastomers (e.g., silicone) or plastics such as Delrin, polycarbonate, acrylic, polystyrene, ABS, or acetal.

The force elements 90 cooperate with the pad or pads 70 (if present) and the flexible ring 50 to create a resistance barrier 110 that exerts barrier forces on the flexible ring 50 in order to resist movement and stretching of the flexible ring 50 in a radially outward direction. The barrier forces may include a radially inward component. Referring to FIGS. 1A, 1D-4, the flexible ring 50 and resistance barrier 110 may be concentrically positioned about the x-axis 54. Due to the force elements 90, the barrier forces may exceed an ordinary reaction force that two objects in contact would ordinarily exert on each other. For example, the barrier forces may bias the flexible ring 50 to a closed state under certain conditions, but need not always do so. Or, the barrier forces may oppose radially outward movement or distortion of the flexible ring 50. Or, the barrier forces may tend to re-center any device 2 inserted through the orifice 52 and manipulated in a radial direction. Even in an equilibrium state, the barrier forces exerted indirectly on a device 2 inserted through the orifice 52 may be relatively large, so as to form a fluid-tight seal between an exterior surface of the device 2 and the flexible ring 50. Depending on the selection and design of the force elements 90, the barrier forces may decrease or increase with the radially outward movement or distortion of the flexible ring 50.

For example, the embodiments of FIGS. 2B-F comprise force elements 90 having spring or elastic force elements 93*a*-93*d* and 94*a*. Accordingly, as radially outward movement or distortion of the flexible ring increases 50, the distortion of the force elements increases, and the barrier force would increase proportionally to the distortion.

As another example, the force elements 90 of FIG. 2A comprise magnetic force elements 91*a*-91*d* with adjacent force elements on adjacent pads 70 (for example, 91*a* and 91*b*) having opposite polarities. As radially outward movement or distortion of the flexible ring 50 causes adjacent force elements, e.g., 91*a* and 91*b* to become separated, the attraction force between two adjacent force elements 90 would decrease as the separation distance increased.

In some embodiments or under certain conditions, the barrier forces may be negligible or zero. For example, the fluid flow control system 10 may be in a first state in which the orifice 52 is free from any devices. At least some embodiments disclosed herein may be designed such that the force elements 90 do not exert barrier forces in this state, or to exert reduced forces. For example, the embodiments of FIGS. 2B-F may be designed so that when the orifice 52 is free from any devices, the force elements 93a-93d and 94a are in a relaxed state and consequently do not exert barrier forces.

Additionally or alternatively, the barrier forces may increase to a nonzero value when movement or distortion of the flexible ring 50 surpasses a predetermined spatial envelope or other threshold, for example, when the flexible ring 50 moves or distorts in a radially outward direction past a predetermined point. Several factors can influence this threshold, including: the material properties of the flexible ring 50; clearance 66 between the flexible ring 50 and any pads 70; clearance 78 between any pads 70 and the housing 30; and the selection, design, and placement of force elements 90 and pads 70.

As one example, the embodiments of FIGS. 2D-2F comprise an elastic force element 94a. This force element 94a may have a resting diameter that exceeds the diameter of the flexible ring 50. Thus, upon radially outward movement or deformation of the flexible ring 50, the force element 94a would not exert any significant force unless such movement or deformation exceeded any slack in the force element 94a and stretched it beyond its resting state.

As another example, shown in FIG. 2A, adjacent pads 70a-70b may be connected by the magnetic force elements 91a-91d discussed above in a first state. A user may manipulate a device 2 within the orifice 52 in a radially-outward direction to a second state, when the radially outward force exceeds the magnetic force connecting the adjacent pads 70a-70b, thereby separating the pads 70a-70b. Beyond that point, the magnetic force elements 91a-91d would tend to draw the adjacent pads 70a-70b together.

In operation, a fluid flow control system 10 according to the present invention may be integrated into a larger assembly, such as introducers, intravenous infusion systems, and urology drainage systems. When the orifice 52 is free of objects (e.g., medical devices), the flexible ring 50 and/or the resistance barrier 110 may cause the orifice 52 to close upon itself into a closed state so that no fluid may escape. This closed state may result from forces—predominantly radially inward forces—that originate from any number of sources, including but not limited to the exterior surface 56, filler material 58, solid element 60, insert, or force elements 90. Such forces may act automatically, e.g., the force elements 90 or the material properties of the exterior surface 56, filler material 58, filler element 60, or insert may bias the orifice 52 to a closed state. In this state, the resistance barrier 110 may automatically exert barrier forces (including a radially inward component), the flexible ring 50 may automatically exert ring forces (including a radially-inward component) to provide a fluid tight seal, or both the resistance barrier 110 and flexible ring 50 may exert forces. Such forces should be sufficiently large to prevent the escape of fluid through the orifice 52, especially fluids under pressures normally encountered in the human anatomy, e.g., the circulatory system.

At some point during a medical procedure, a user may insert a device 2, such as a catheter or guidewire, through the orifice 52, as shown in FIG. 1C. In order to pass, the device 2 may push through the closed orifice 52 by overcoming any barrier forces and/or ring forces. It may be desirable for the barrier forces to be zero or relatively low in this state, and also for the ring forces to be relatively low in order to facilitate device insertion. To facilitate passage, the portion of the exterior surface 56 of the flexible ring 50 proximate the orifice 52 and/or the device 2 may be coated with a surface coating. The flexible ring 50 is allowed to expand or distort to accommodate the device 2, and may accommodate a wide range of devices. It is also possible for the flexible ring 50 to accommodate more than one device 2 through the orifice 52 simultaneously. When the device 2 is inserted, the flexible ring 50 may exert ring forces on the exterior surface of the device 2 to form a fluid-tight seal, for example a radially-inward ring force. Depending on the diameter of the device 2 and the design of the particular embodiment, the resistance barrier 110 may exert barrier forces on the flexible ring 50, such as a radially-inward barrier force, which is transferred to the device 2 and further helps form a fluid-tight seal. In all cases, the barrier forces and ring forces cooperate to provide a fluid-tight seal regardless of the device diameter or position of the device 2 relative to the housing 30. However, the barrier forces and ring forces are ideally not so great as to inhibit the insertion, removal, or manipulation of devices.

During a medical procedure, a user may manipulate the device 2 in a radially-outward direction. This action causes the flexible ring 50 to move and/or distort, in particular the portion of the flexible ring 50 near the orifice 52. During such a movement, the fluid flow control system 10 may cause the leading and trailing parts of the flexible ring 50 to move or distort together in order to maintain a fluid-tight seal around the device 2. For example, the resistance barrier 110 may exert a radially-inward barrier force on the leading surface of the device 2 in order to resist radially-outward movement; simultaneously, the resistance barrier 110 may exert a barrier force on the trailing surface of the device 2 in order to maintain a fluid-tight seal around the device during periods when the user manipulates the device 2 in a radially outward manner. Additionally or alternatively, the flexible ring 50 may exert ring forces on the leading and trailing surfaces of the device 2, which ring forces may be radially inward and/or outward, depending on the position of the device and region of the device 2 on which the flexible ring 50 acts.

During the procedure, the first and second surfaces 36, 38 of the housing 30 prevent x-axis movement or distortion of components of the fluid flow control system 10. In particular, the housing 30 prevents at least a portion of the flexible ring 50 from "bulging" in the x-direction, which could reduce the efficacy of the barrier forces and ring forces. Although the housing 30 prevents x-axis movement of the components, the internal components may move and distort radially within a limited spatial envelope. In particular, the flexible ring 50, force elements 90, and pads 70 may move by a clearance distance 78 between the pad 70 and the housing 30. In embodiments without a pad 70, the flexible ring 50 may move radially by a clearance distance 66 between an exterior surface 56 of the flexible ring 50 and the housing 30. Additionally, the flexible ring 50 may distort, thereby permitting the user additional range of movement in radial directions.

The fluid flow control systems of the present invention offers numerous advantages. In particular, the systems automatically provide an effective fluid seal without a separate human step, e.g., rotating a handle. This advantageously eliminates one complication of medical procedures and reduces the opportunity for human error. Additionally, the fluid flow control systems provide an effective fluid seal around a range of device sizes and automatically adjust for different devices without a separate human step or performance degradation. During procedures requiring multiple devices of different sizes, the present fluid flow control systems provide improved performance over prior art systems, which are known to accommodate a limited range of device sizes. Such prior art systems are also known to permit fluid loss due to degradation of material properties, for example the loss of elasticity and homogeneity of silicone discs. The fluid flow control systems of the present invention do not suffer from this drawback. Altogether, the advantages of the present fluid flow control systems contribute to reduced fluid loss, reduced error rate, and shorter procedure times.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A fluid flow control system, comprising: a housing; a flexible ring located within the housing, the flexible ring having an orifice for receiving a device; and a resistance barrier adjacent to an exterior surface of the flexible ring, the resistance barrier comprising at least one force element and at least one pad, wherein the resistance barrier selectively exerts a radially-inward barrier force upon the exterior surface of the flexible ring and towards the orifice, wherein the at least one pad redirects a force generated by the at least one force element, wherein the flexible ring is a single continuous ring, and wherein the flexible ring is filled with a filler material having flexible properties.

2. The fluid flow control system of claim 1, wherein the resistance barrier automatically exerts the barrier force.

3. The fluid flow control system of claim 1, wherein the barrier force is zero when the fluid flow control system is in a first state.

4. The fluid flow control system of claim 1, wherein the flexible ring exerts a ring force independent of the barrier force, wherein the ring force comprises a radially-inward component.

5. The fluid flow control system of claim 4, wherein the ring force is less than the barrier force in a first state.

6. The fluid flow control system of claim 4, wherein the ring force is zero when the fluid flow control system is in a first state.

7. The fluid flow control system of claim 1, wherein the at least one pad comprises a first pad and a second pad.

8. The fluid flow control system of claim 7, wherein the force element creates an attraction force between the first pad and the second pad.

9. The fluid flow control system of claim 7, wherein the force element forms a physical connection between the first and second pads.

10. The fluid flow control system of claim 1, wherein the force element comprises at least one of: a magnet, a spring, an elastic component, a pneumatic cylinder, a hydraulic cylinder, or an electric actuator.

11. A fluid flow control system, comprising:
a flexible ring comprising a surface and defining an orifice for receiving a device, the orifice traversed by an axis;
a resistance barrier adjacent to the flexible ring and comprising at least one force element and at least one pad; and
a channel formed in a housing about the axis,
wherein the channel prevents movement of the flexible ring in a direction parallel to the axis,
wherein a clearance space is provided between an interior surface of the housing and an exterior surface of the flexible ring, wherein the exterior surface of the flexible ring can move radially outward in the clearance space,
wherein the flexible ring is a single continuous ring, and
wherein both the force element and the at least one pad are radially aligned with a part of the orifice that can close around the device.

12. The fluid flow control system of claim 11, wherein the channel has a substantially uniform cross section about the axis.

13. The fluid flow control system of claim 11, wherein the surface is attached to the housing.

14. The fluid flow control system of claim 11,
wherein the flexible ring comprises a first band comprising a circumferential channel,
wherein the resistance barrier comprises a second band residing with the circumferential channel.

15. The fluid flow control system of claim 11, wherein the surface encloses a filler material.

16. The fluid flow control system of claim 15, wherein the filler material comprises a polymer.

17. The fluid flow control system of claim 15, wherein the filler material comprises at least one of: hyaluronic acid, polymethylmethacrylate, or polyacrylamide.

18. The fluid flow control system of claim 11, wherein the flexible ring and the resistance barrier are concentrically assembled within the channel.

19. A method for controlling fluid flow during a medical procedure, the method comprising:
manipulating a device through an orifice of a flexible ring in at least a longitudinal direction; and
utilizing a resistance barrier comprising at least one force element and at least one pad to automatically exert a radially-inward sealing force on the flexible ring,
wherein the sealing force provided by the at least one force element is transferred towards the orifice to provide a seal around the device,
wherein the flexible ring is a single continuous ring, and
wherein both the force element and the at least one pad are radially aligned with a part of the orifice that can close around the device.

20. The method of claim 19, further comprising:
preventing movement of a portion of the flexible ring in the longitudinal direction; and
limiting movement of the flexible ring in a radially-outward direction.

* * * * *